United States Patent [19]

Suld et al.

[11] 4,237,310

[45] * Dec. 2, 1980

[54] CO-OXIDATION OF METHYL BENZENES AND BENZALDEHYDE TO PHENOLICS AND FORMALDEHYDE

[75] Inventors: George Suld, Springfield; James E. Lyons, Wallingford; Robert W. Shinn, Aston, all of Pa.

[73] Assignee: Suntech, Inc., Philadelphia, Pa.

[*] Notice: The portion of the term of this patent subsequent to Dec. 2, 1997, has been disclaimed.

[21] Appl. No.: 957,614

[22] Filed: Nov. 3, 1978

[51] Int. Cl.$^3$ .................... C07C 67/39; C07C 69/157
[52] U.S. Cl. ................................. 560/131; 560/241
[58] Field of Search ......................... 560/131

[56] References Cited

U.S. PATENT DOCUMENTS

| | | | |
|---|---|---|---|
| 3,772,383 | 11/1973 | Kominami et al. | 560/131 |
| 4,056,572 | 11/1977 | Bashkirov et al. | 560/131 |

OTHER PUBLICATIONS

Grozhan et al., Doklady Akad. Nauk, SSSR, 204 (4), pp. 872-873 (1972).

Primary Examiner—Jane S. Myers
Attorney, Agent, or Firm—J. Edward Hess; Donald R. Johnson; Stanford M. Back

[57] ABSTRACT

The oxidation of methyl benzenes, such as toluene, with air or oxygen in the presence of acetic anhydride and sulfuric acid catalyst to form a phenolic acetate and methylene diacetate may be carried out under mild conditions when small amounts of benzaldehyde are added to the reaction.

The resulting acetates may then be pyrolyzed to yield phenolic compounds and formaldehyde, respectively.

9 Claims, No Drawings

CO-OXIDATION OF METHYL BENZENES AND BENZALDEHYDE TO PHENOLICS AND FORMALDEHYDE

BACKGROUND OF THE INVENTION

This invention relates to a novel process for the oxidation of methyl benzenes. More particularly, this invention relates to an improved process for the oxidation of methyl benzenes with air or oxygen in the presence of acetic anhydride and sulfuric acid under mild conditions to form a phenolic acetate and methylene diacetate. These compounds may then be converted to the corresponding phenolic compound and formaldehyde or paraformaldehyde by, for example, pyrolysis.

Earlier work of Grozhan et al., (Doklady Akad. Nauk, SSSR, 204, No. 4,872) established that acid catalyzed oxidation of toluene at high temperature and pressure in acetic anhydride followed by saponification of the reaction product gave phenol in modest yield. More recent work of Lyons, Suld and Shinn application Ser. No. 945,747 has shown that phenyl acetate, methylene diacetate and acetic acid are the major products of the acid catalyzed air oxidation of toluene in acetic anhydride. Despite recent improvements using catalysts initiators and promoters and acetic acid as a solvent this prior work has necessitated high temperatures and pressures to achieve reasonable rates and yields.

SUMMARY OF THE INVENTION

We have now discovered that the acid-catalyzed oxidation of methyl benzenes in acetic anhydride to form a phenolic acetate, methylene diacetate, and acetic acid occurs at convenient rates and good yields under mild conditions of temperature and pressure when the reaction is carried out in the presence of small amounts of benzaldehyde. The reaction proceeds readily at temperatures as low as 100° C. and oxygen pressure of 1 atmosphere. The resulting acetates may then be converted to the respective phenolic compounds and formaldehyde or paraformaldehyde by pyrolysis or the like.

DESCRIPTION OF THE INVENTION

The process, using the oxidation of toluene as an example, may be illustrated by the following equation:

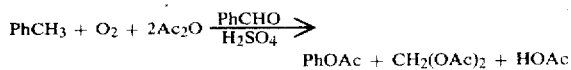

$$PhCH_3 + O_2 + 2Ac_2O \xrightarrow[H_2SO_4]{PhCHO} PhOAc + CH_2(OAc)_2 + HOAc$$

It will be understood, however, that this novel method is equally applicable to other methyl benzenes such as xylenes and trimethyl benzenes, e.g. mesitylene and pseudocumene.

In general, the process is carried out by oxidizing the desired methyl benzene with air or oxygen in the liquid phase at pressures of at least 1 atmosphere and at temperatures as low as 80° C. to form equimolar amounts of a phenolic acetate and methylene diacetate, together with acetic acid and lesser amounts of certain methyl-benzene-derived by-products. The phenolic acetate and methylene diacetate, following separation, may then be pyrolyzed to form the corresponding phenolic compound and formaldehyde respectively, while the acetic acid may be routinely converted to acetic anhydride and recycled to the oxidation step.

It will thus be seen that as contrasted with the prior art, this invention is particularly characterized by the surprising discovery that the above-described oxidation can be carried out under very mild reaction conditions by simply adding small amounts of benzaldehyde to the reaction.

As aforementioned, the reactants are methyl benzenes, such as toluene, xylene (ortho, meta, or para) and trimethylbenzenes such as mesitylene and pseudocumene, together with acetic anhydride and oxygen or air, in the presence of a strong acid catalyst, preferably $H_2SO_4$, and, as the novel feature of this invention, benzaldehyde. The weight ratio of methyl benzene to acetic anhydride should desirably be in the range of from about 50:1 to 1:10, and preferably 10:1 to 2:1, while the weight ratio of $H_2SO_4$ to methyl benzene should generally be from about $5 \times 10^{-4}$ to $1 \times 10^{-2}$, and preferably $1 \times 10^{-3}$ to $5 \times 10^{-3}$.

The amount of benzaldehyde employed is about 0.01 to 1.0 moles, and preferably 0.05 to 0.10 moles, per mole of methyl benzene.

If desired, the reaction may be run in excess methyl benzene reactant as a solvent, or in a suitable organic solvent such as benzene, chlorobenzene, or acetic acid. The latter is preferred inasmuch as increased selectivities are observed. Desirably, for more rapid reactions, in acetic acid, promoters such as Dry Caro's acid should be employed. The acetic acid, when used, should be present in amounts of 1–30, preferably 2–10 volumes per volume of acetic anhydride based on the amount of acetic anhydride used.

It has further been found that persulfate promotors such as sodium persulfate, potassium persulfate, persulfuric acid or Dry Caro's acid are particularly effective promoters for this oxidation reaction. These promoters are desirably used in amounts of from about $10^{-3}$ to $10^{-1}$ g per gram of methyl benzene.

The reaction, which employs oxygen or equivalent amounts of air, can, and should, as aforestated, be carried out under relatively mild conditions, i.e. at temperatures of at least 80° C., up to about 150° C., and most desirably at about 90°–120° C., and at air or $O_2$ pressures of at least 1 atmosphere, up to about 10 atmospheres, with the lower ranges of both pressure and temperature being preferred.

The reaction product containing the phenolic acetate and methylene diacetate, as well as acetic acid, and lesser amounts of methyl benzene derived by-products, and the like is then routinely heated to remove the acid catalyst, following which the two acetate products may be separated by distillation under vacuum.

The recovered phenolic acetate is then converted to phenol, cresol or the like by pyrolysis. This is conventionally achieved by heating the acetate at temperatures of from about 500° to 1000° C., preferably at about 625° C., and preferably in the presence of a catalyst such as triethyl phosphate and recovering the desired product by routine means.

In a like manner, the pyrolysis of methylene diacetate yields formaldehyde and acetic anhydride. This pyrolysis is conventionally carried out in one step in a homogeneous gas phase reaction, at about 450°–550° C. under reduced pressure.

The acetic acid recovered from the oxidation of the alkyl benzene may then be converted to acetic anhydride for recycling to the initial oxidation step. This may readily be achieved e.g. by contacting ketene with acetic acid at room temperature in the liquid phase.

The following examples are provided solely for purposes of illustrating but not limiting the novel process of this invention.

EXAMPLE 1

Into a manometric gas-recirculation oxidation apparatus were charged following reactants:

| | |
|---|---|
| Toluene | 21.4 ml |
| Acetic Anhydride | 4.0 ml |
| Sulfuric Acid | 1 drop (ca 0.03 g) |

Air in the reaction flask was replaced with nitrogen and the reaction mixture was heated to 101°–3° C. When the temperature reached the desired level nitrogen was replaced by pure oxygen and the gas recirculating pump was started, charging oxygen through the liquid at 300–400 ml/min. The gas uptake was measured in the mercury filled buret by a/displacement method. Liquid samples were withdrawn from the reaction vessel and analyzed by standard gas chromatographic techniques. No measurable oxygen uptake occurred under these conditions and no oxidation product(s) were found in the reaction mixture. After 2 hours and 25 minutes on stream 0.49 g of benzoyl peroxide, a free radical initiator, was added to the reaction mixture and the reaction was continued for additional 2 hours and 35 minutes. A slow oxygen uptake, a total of 185 ml was recorded as a function of time.

At the end of this period, toluene oxidation products were analyzed by gas chromatography. The wt.% values given are normalized on the basis of the following compounds:

Methylene diacetate (MDA), benzaldehyde (BAL), phenyl acetate (PA), benzyl acetate (BAC), phenyl hemiformal acetate (PHF), and other, unidentified products appearing within the same GC scanning range.

Although benzaldehyde is an added reagent it is conveniently included in the product analysis since it appears within the GC scanning range of toluene oxidation products.

The reaction mixture contained, calculated on the basis of the normalized product scans less than 1% of methylene diacetate (MDA) and <3% phenyl acetate (PA). The bulk of the oxidized product was benzyl acetate (BAC), 28%, and benzylidine diacetate (BDA) 26%, together with a number of unidentified products.

EXAMPLE 2

Into the reactor was charged:

| | |
|---|---|
| Toluene | 21.4 ml |
| Acetic Anhydride | 4.0 ml |
| Sulfuric Acid | 1 drop (0.03 g) |

The reaction was carried out in the same manner as in Example 1 for 1 hour. There was no oxygen absorption over this time period, at the end of which 1.0 ml. benzaldehyde and 3 drops of sulfuric acid were added. The oxygen absorption commenced after a few minutes; at the end of the reaction after total of 3 hours, 50 minutes 636 ml oxygen had been absorbed. Analysis of the liquid oxidation product carried out as described in Example 1 showed 10% MDA and 11% PA were present, together with 20% BAC and 12% phenylhemiformal acetate (PHF), a precursor of both PA and MDA.

EXAMPLE 3

Into the reactor was charged:
Toluene—21.4 ml
Acetic Anhydride—4.0 ml
Sulfuric Acid—1 drop (0.03 g)

The reaction was carried out initially as in Example 1 for 4 hours and 16 minutes with only negligible oxygen uptake recorded over this time period. At the end of this period 1.0 ml. of benzaldehyde and 0.56 g. of potassium persulfate were added to the reaction mixture. The oxygen uptake commenced after a few minutes and a total of 712 ml oxygen were absorbed by the end of 7 hours and 33 minutes. The toluene conversion, based on oxygen absorbed was ca 10%. The liquid product analysis as determined in Example 1, showed 10% MDA, 12% PA, 16% BAC and 10% PHF among the oxidation products of toluene.

EXAMPLE 4

Into the reactor was charged:

| | |
|---|---|
| Toluene | 21.4 ml |
| Acetic Anhydride | 4.0 ml |
| Acetic Acid | 12.0 ml |
| Benzaldehyde | 2.0 ml |
| Dry Caro's Acid | 0.25 g |
| Sulfuric Acid | 3 drops (~0.1 g) |

Reaction was carried out initially as in Example 1 with all the ingredientss added at the start and after 2 hours and 20 minutes a liquid product sample was analyzed: 12% MDA, 11% PA and 9.5% of PHF were present in the product. The reaction was continued for a total of 6 hours and 55 minutes. At 3 hours and 34 minutes 2.0 ml of acetic anhydride and at 6 hours and 4 minutes 0.25 g of Dry Carco's acid were added. The final liquid oxidation product, analyzed as in Example 1, contained 20% MDA, 19% PA, 13;1 % BAC and 4% PHF. The total oxygen uptake was 490 ml with 1.6 m mole $CO_2$ produced in the reaction.

EXAMPLE 5

Into the reactor was charged:

| | |
|---|---|
| Toluene | 21.4 ml |
| Acetic Anhydride | 4.0 ml |
| Acetic Acid | 12.0 ml |
| Benzaldehyde | 1.0 ml |
| Co-stearate | 7.4 mg. |

The oxidation reaction was carried out initially as in Example 1. At the end of 3 hours and 15 minutes 514 ml oxygen had been absorbed. The product, analyzed as in Example 1, contained 16% MDA, 5% PA and 7% PHF.

EXAMPLE 6

Into the reactor was charged:

| | |
|---|---|
| Toluene | 21.4 ml |
| Acetic Anhydride | 8.0 ml |
| Acetic Acid | 12.0 ml |
| Benzaldehyde | 1.0 ml |
| Sodium Perborate Tetrahydrate | 1.54 g. |
| Sulfuric Acid | 3 drops (~0.1 g.) |

Reaction was carried out as in Example 1. After 3 hours and 22 minutes 780 ml oxygen had been absorbed. Analysis of the liquid oxidation product, as in Example 1, showed 14% MDA <2% PA, 37% benzaldehyde and 34% other products.

EXAMPLE 7

Into the reactor was charged:

| | |
|---|---|
| Toluene | 42.8 ml |

| | |
|---|---|
| Acetic Anhydride | 8.0 ml |
| Sulfuric Acid | 2 drops (0.07 g) |

Reaction was carried out initially as in Example 1. The following reactants were added in the course of the oxidation reaction at given time intervals: cyclohexanone, 0.6 ml at 35 min. over a 40 min. period; azobisisobutyronitrile (AIBN), 66 mg. at 186 min.; potassium persulfate, 0.20 g. at 300 min. The reaction was carried out for a total of 10 hours and 27 minutes whereby a total oxygen uptake was 790 ml. Only traces of the desired products PA and MDA were found among the oxidation products.

EXAMPLE 8

Into the reactor was charged:

| | |
|---|---|
| p-Xylene | 24.1 ml |
| Acetic Anhydride | 4.0 ml |
| Benzaldehyde | 1.0 ml |
| Dry Caro's Acid | 0.5 g |
| Sulfuric Acid | 3 drops (~0.1 g) |
| chlorobenzene | 1.0 ml |

(as internal standard)

The reaction was carried out initially as in Example 1; the reaction temperature was 104°–7° and after 4 hours the total oxygen uptake was 582 ml. Analysis of the oxidized product showed the presence of p-cresyl acetate 28%, and methylene diacetate 16%, 7.5 m mole of carbon dioxide was also formed.

EXAMPLE 9

Into a 300 ml rocker bomb was charged:

| | |
|---|---|
| Toluene | 43.0 ml |
| Acetic Anhydride | 8.0 ml |
| Benzaldehyde | 2.0 ml |
| Dry Caro's Acid | 1.0 g |
| Sulfuric Acid | 0.11 g |

The bomb was pressurized with 120 psi oxygen and 170 psi nitrogen, i.e. total 290 psi at room temperature and was heated to 120° over a 30 minutes period. The reactor was heated at 115°–120° for 3 hours, 35 minutes, resulting in the pressure drop of 65 psi. Analysis of the oxidation product, as in Example 1, showed 17% PA, 24% MDA and 8% PHF.

EXAMPLE 10

Into a 300 ml rocker bomb was charged:

| | |
|---|---|
| Toluene | 50 ml |
| Acetic Anhydride | 11.4 ml |
| Sulfuric Acid | 0.11 g |

The bomb was pressurized with 30 psi oxygen and 145 psi nitrogen, i.e. total of 175 psi at room temperature. The reactor was heated at 130° for an 8 hour period; no pressure drop was observed and no oxidation products were detected in the reaction mixture at the end of the reaction.

EXAMPLE 11

Pyrolysis of methylene diacetate to paraformaldehyde and acetic anhydride can be accomplished thermally at about 500° C. in a known manner.

Alternatively, the catalytic pyrolysis of methylene diacetate may be carried out at about 300° C. in the presence of a catalyst composed of 5% sodium chloride mixed with silica gel, dried and calcined. The methylene diacetate, dissolved in n-hexane, is passed through a passified tubular reactor packed with the catalyst at a space velocity of 900 hr$^{-1}$ and a temperature of 300° C. Paraformaldehyde and acetic anhydride condense downstream and are separated routinely. Selectivities exceed 93% for acetic anhydride and 95% for methylene diacetate.

EXAMPLE 12

Pyrolysis of phenyl acetate to phenol and ketene is accomplished thermally at 625° C. by passing it through a well-conditioned tubular reactor. The effluent is condensed to give 84% yield of phenol and 89% yield of ketene.

The reaction may be carried out at a somewhat lower temperature in the presence of triethyl phosphate catalyst at space velocities of between 900 and 1000 hr$^{-1}$. Yields in excess of 90% are obtained.

Cresyl acetate may be converted in a like manner to cresol.

The results of the foregoing Examples can better be appreciated in light of the following discussion:

Example 1 shows that essentially no oxidation of toluene occurs in the presence of acetic anhydride and sulfuric at the pressures and temperatures given. If further shows that upon addition of a free radical chain initiator such as benzoyl peroxide, a slow oxidation reaction takes place but the predominant products are not the desired phenyl acetate (PA) and methylene diacetate (MDA) which are both present in amounts less than 3%.

Example 2 shows that addition of benzaldehyde to toluene plus acetic anhydride plus sulfuric acid causes a resonably rapid reaction to occur, whereby ~10% MDA, 11% PA and 12% PHF, a precursor of MDA and PA, are formed.

Example 4 shows that the oxidation of toluene in the presence of acetic anhydride, and acetic acid, benzaldehyde, dry Caro's acid, and sulfuric acid gives a superior selectivity to PA and MDA. The key factor here would appear to be the addition of Caro's acid plus acetic acid to other previously used reactants.

Example 5 shows that addition of a conventional toluene oxidation catalyst i.e. a cobalt salt, does not promote a selective reaction since only 5% of PA was found together with 11% BAC.

Example 6 shows that another strong, non-heavy metal oxidant such as sodium perborate does not promote the formation of PA since less than 2% of the latter was present.

Example 7 shows that use of another carbonyl-containing promoter, cyclohexanone, instead of benzaldehyde does not result in the formation of the desired products, PA and MDA.

Example 8 shows that benzaldehyde can promote the oxidation of higher homologs of toluene e.g., xylenes. In the case of p-xylene, p-cresyl acetate is formed.

Example 9 shows that when co-oxidation of toluene and benzaldehyde is carried out at 120° i.e. at low temperature and somewhat elevated pressure of oxygen (120 psi), substantial quantities of both PA and MDA are obtained.

Example 10 shows that no oxidation occurs at 130° in the absence of benzaldehyde.

Examples 11 and 12 illustrate the conversion of phenyl acetate and methylene diacetate to phenol and formaldehyde respectively.

We claim:

1. A process for the oxidation of methyl benzenes under mild reaction conditions to form phenolic acetates and methylene diacetate which comprises contacting said methyl benzenes with air or oxygen, and acetic anhydride, in the presence of a strong acid catalyst and benzaldehyde at temperatures of from about 80° C. to 150° C. and pressures of at least 1 atmosphere, and recovering the phenolic acetate and methylene diacetate, said benzaldehyde being present in amounts of from about 0.01-1.0 mole based on the methyl benzene.

2. The process of claim 1 wherein the acid catalyst is $H_2SO_4$.

3. The process of claim 1 wherein the pressure is from about 1 to 10 atmospheres.

4. The process of claim 1 wherein a suitable organic solvent is employed.

5. The process of claim 4 wherein the solvent is acetic acid in the presence of a promoter.

6. The process of claim 5 wherein the reaction is carried out in the presence of a persulfate promoter.

7. The process of claim 6 wherein the promoter is Dry Caro's acid.

8. The process of claim 1 wherein the methyl benzene is toluene and the products are phenyl acetate and methylene diacetate.

9. The process of claim 1 wherein the methyl benzene is a xylene and the products are a cresyl acetate and methylene diacetate.

* * * * *